US006653294B2

(12) United States Patent
Hwang et al.

(10) Patent No.: US 6,653,294 B2
(45) Date of Patent: Nov. 25, 2003

(54) USE OF CHITINOUS MATERIALS FOR INHIBITING CELLULAR NITRIC OXIDE PRODUCTION

(75) Inventors: Shiaw-Min Hwang, Hsinchu (TW); Chiung-Yun Chen, Hsinchu (TW); Shan-Shan Chen, Hsinchu (TW); Jian-Chyi Chen, Muili County (TW)

(73) Assignee: Food Industry Research & Development Institute, Hsinchu (TW)

( * ) Notice: Subject to any disclaimer, the term of this patent is extended or adjusted under 35 U.S.C. 154(b) by 290 days.

(21) Appl. No.: 09/733,636

(22) Filed: Dec. 8, 2000

(65) Prior Publication Data

US 2001/0036934 A1 Nov. 1, 2001

Related U.S. Application Data

(63) Continuation-in-part of application No. 09/515,420, filed on Feb. 29, 2000, now abandoned.

(51) Int. Cl.⁷ ...................... A61K 37/715; A61K 31/70
(52) U.S. Cl. ............................. 514/55; 514/61; 514/62
(58) Field of Search ............................. 514/55, 61, 62

(56) References Cited

U.S. PATENT DOCUMENTS 3,903,268 A 9/1975 Balassa ...................... 424/180

FOREIGN PATENT DOCUMENTS

| EP | 0382210 | 8/1990 |
|----|---------|--------|
| JP | 08040915 | 2/1996 |
| JP | 08165243 | 6/1996 |
| JP | 09059164 | 3/1997 |
| JP | 09087302 | 3/1997 |
| WO | WO 97/17977 | 5/1997 |

OTHER PUBLICATIONS

Hwang S.–M., et al "Chitinous materials inhibit nitric oxide prodction . . . " Biochem. Biophys. Res. Comm., 2000, vol 271, pp. 229–233.*
Peluso, G. et al "Chitosan–mediated stimulation of macrophase function" Biomaterials, 1994, vol 15, No. 15, pp. 1215–1220.*
Rementeria A., et al "Resistance to candidiasis and macrophage activity in chitin–treated mice" FEMS Immunol. Med. Microbiol., 1997, vol 19, pp. 223–230.*
Peluso et al., "Chitosan–mediated stimulation of macrophage function," Biomaterials, pp. 1215–1220, 1994.
Nishimura et al., "Effect of chitin heparinoids on the activation of peritoneal macrophages and on the production of monokines in mice," Mol. Biother., pp. 115–120, 1990.
Tsai et al., "Antibacterial Activity of Shrimp Chitosan against *Escherichia coli*," Journal of Food Protection, pp. 239–243, 1999.
Su et al., "Fungal mycellia as the source of chitin and polysaccharides and their applications as skin substitutes," Biomaterials, pp. 1169–1174, 1997.
Austin et al., "Chitin: New Facets of Research," Science, pp. 739–753, 1981.
Tachibana et al., "The Use of Chitin as a New Absorbable Suture Material–An Experimental Study," Japanese Journal of Surgery, pp. 533–539, 1988.
Nishimura et al., "Stimulation of cytokine production in mice using deacetylated chitin," Vaccine, pp. 151–156, 1986.
Yalpani et al., "Antimicrobial Activity of Some Chitosan Derivatives," In: Advances in Chitin and Chitosan, Brine et al. eds., Elsevier Applied Science, pp. 543–548 1992.
Biagini et al., "Biological Materials for Wound Healing," In: Advances in Chitin and Chitosan, Brine et al., eds., Elsevier Applied Science, pp. 16–24, 1992.
Sashiwa et al., "Lasozyme Susceptibility of partially deacetylated chitin," Int. J. Biol. Macromol, Vol. 12, pp. 295–296, 1990.
Su et al., "Development of Fungal mycelia as skin substitutes: Effects on wound healing and fibroblast," Biomaterials, vol. 20, pp. 61–68, 1999.
Kifune, "Clinical Application of Chitin Artificial Skin," In: Advances in Chitin and Chitosan, Brine et al. eds., Elsevier Applied Science, pp. 9–15, 1992.
Okamoto et al., "Application of Chitin and Chitosan in Small Animals," In: Advances in Chitin and Chitosan, Brine et al. eds., Elsevier Applied Science, pp. 70–79, 1991.
Minami et al., "Application of Chitin and Chitosan in Large Animal Practice," In: Advances in Chitin and Chitosan, Brine et al. eds., Elsevier Applied Science, pp. 60–69, 1991.
Johnson et al., "In Vivo Tissue Response to Implanted Chitosan Glutamate," In: Advances in Chitin and Chitosan, Brine et al. eds., Elsevier Applied Science, pp. 3–8, 1991.
Knapczyk et al., "Pharmaceutical Dosage Forms With Chitosan," In: Chitin and Chitosan, Skjåk–Bræk et al. eds., Elsevier Applied Science, pp. 665–669, 1988.
Shigemasa et al., "Applications of Chitin and Chitosan for Biomaterials," In: Proceedings of the third Asia–Pacific Chitin and Chitosan Symposium, Chen et al. eds., Elsevier Applied Science, pp. 47–54, 1998.
Shen et al., "Effects of Chitosan on the healing of tooth–extraction–wound: A preliminary histophathological study in rats," In: Proceedings of the third Asia–Pacific Chitin and Chitosan Symposium, Chen et al. eds., Elsevier Applied Science, pp. 284–290, 1998.
Caplus abstract: Okamoto, Y. et al, "Effect of chitin and . . . ," Kichin, Kitosan Kenkyu, 5(2):124–125.
Rementerial et al., "Resistance to candiasis . . . ," FEMS Immun and Med. Microbiol., 19:223–230.

* cited by examiner

*Primary Examiner*—Kathleen K. Fonda
*Assistant Examiner*—Leigh C. Maier
(74) *Attorney, Agent, or Firm*—Fish & Richardson P.C.

(57) ABSTRACT

The invention relates to a method of reducing nitric oxide production by a cell in vitro or in a mammal by a cell by contacting the cell with chitosan or its derivatives in an amount effective to reduce nitric oxide production in the cell.

20 Claims, No Drawings

USE OF CHITINOUS MATERIALS FOR INHIBITING CELLULAR NITRIC OXIDE PRODUCTION

CROSS-REFERENCE TO RELATED APPLICATIONS

This application is a continuation-in-part of U.S. Ser. No. 09/515,420, filed Feb. 29, 2000, now abandoned.

BACKGROUND OF THE INVENTION

Nitric oxide (NO) is associated with an array of diverse biological phenomena, such as inflammation, septic shock, adverse consequences of ischemia and reperfusion injury, hypotension, cell development, and apoptosis. Inflammation of a tissue in vivo is often characterized by the infiltration or presence of activated macrophages, which in turn produce NO as a mediator of vasodilation in the inflammation process. Thus, inflammation can be ameliorated by decreasing NO production by cells such as macrophages.

SUMMARY OF THE INVENTION

Chitosan is an acid-soluble polymer of β-(1,4)-D-glucosamine. Chitin is a relatively insoluble, acetylated form of chitosan. Chitin, chitosan, and derivatives thereof are used in a number of industrial applications, including the production of viscosity control agents, adhesives, chromatography carriers, paper-strengthening agents, flocculent agents, food additives, drugs, and cosmetics.

The invention is based on the surprising result that chitosan and derivatives thereof can inhibit cellular NO production. This result was unexpected because it had been reported that chitosan stimulated NO production by rat macrophages in vitro (Peluso et al., Biomaterials 15:1215–1220, 1994). However, it appears that previous studies may have used preparations of chitosan that are contaminated with endotoxin or other agents that cause an increase in NO production. Therefore, the invention is directed to endotoxin-free preparations of chitin or chitosan.

Accordingly, the invention features a method of reducing NO production in a subject (e.g., a mouse, mammal, or human) by identifying a subject in which reduction of NO production is desired; and administering to the subject an amount of an endotoxin-free composition comprising chitosan sufficient to reduce NO production in the subject. The composition can be administered locally (e.g., at a site of inflammation in the subject, such as an arthritic joint), systemically (e.g., intravenously), or as part of an implantable device (e.g., a surgical prosthesis such as a wound dressing, or a device that provides for slow release of the composition). A reduction of NO production can be desirable when NO production is abnormally elevated; or when NO production is normal, but an NO production level below normal provides a benefit to the mammal.

The invention also includes a method of reducing NO production in a cell by contacting the cell with a composition comprising chitosan in an amount sufficient to reduce NO production in the cell.

The term "composition comprising chitosan" as used herein means (1) chitosan; (2) a derivative of chitosan, including partially acetylated chitosan, fully acetylated chitosan to form chitin, and chitosan formed of polysaccharides (e.g., of 5 to 10, or 5 or 6 sugar or glucosamine residues); and (3) a mixture of (1) or (2) or both, and containing one or more additives (e.g., a carrier) or other bioactive compounds, as discussed below. In general, chitosan is produced by deacetylating chitin. However, the above definition is meant to encompass both chitin and chitosan for efficiency's sake.

The term "endotoxin-free" refers to a composition that does not test positive in any one of a number of endotoxin or lipopolysaccharide assays known in the art, such as described in Nakamura et al., Nephrol. Dial. Transplant. 15:1928–1934, 2000; Pang et al., J. Neurosci. Res. 62:510–20, 2000; or Schoeffel et al., Am. J. Surg. 180:65–72, 2000.

The methods of the invention can be used to treat or prevent any disease or condition in which NO production or its consequent physiological effects are undesirable. Such diseases or conditions are discussed below. In addition, the methods of the invention can be used for in vitro or in vivo animal model testing or screening of the efficacy of chitosan or derivatives thereof as a drug for treating various conditions, such as inflammation. Successful screening of effective and noneffective derivatives of chitin or chitosan is described in the Examples below (see, e.g., Tables 1 and 2).

Other features or advantages of the present invention will be apparent from the following detailed description, and also from the claims.

DETAILED DESCRIPTION

The invention relates to the administration of a composition including chitosan to a subject for the treatment or prevention of any condition or disease that is mediated by cellular NO production. Various methods for carrying out the invention are discussed below.

Specific diseases or disorders treatable with the composition include an inflammatory disease or disorder, hypotension, septic or traumatic shock, chronic hypotension, or priapism. Accordingly, the method of the invention can include administration of an amount of a vasoconstrictor, which together with chitosan or a derivative thereof, is effective to increase blood pressure. Suitable vasoconstrictors include epinephrine, norepinephrine, vasopressin, $N^G$-monomethyl-L-arginine, $N^G$-nitroarginine methyl ester, and prostagladin. The methods can also be used to inhibit smooth muscle cell relaxation in response to NO. Thus, in general, inhibition of NO production leads to many therapeutic benefits, either as the primary active ingredient in drug therapy or as an adjunct to another drug such as a steroid, antibody, or peptide hormone. In addition, the composition can be administered when NO production is normal, but an NO production level below normal provides a benefit to the mammal. For example, it may be desirable to decrease the normal vasodilation of endothelium in the kidney tubules because a patient is dehydrated.

Inflammation can involve a cell-mediated immune response, with release of toxic molecules such as NO. A cell-mediated immune response can be beneficial, e.g., for destroying infectious microorganisms such as bacteria and parasites, and for eliminating cancerous or infected cells. However, inflammation can become chronic, autoimmune, or detrimental, such as in asthma, cirrhosis, inflammatory bowel disease, and arthritis.

NO has been associated with the adverse effects of ischemic events. Ischemia or hypoxia is a particularly serious problem when it occurs in the heart, e.g., as a consequence of a myocardial infarct or after balloon angioplasty. Ischemia in the brain is also a serious but common problem associated with stroke. Thus, the methods of the invention can further include administration of a drug (e.g., tissue plasminogen activator or streptokinase) designed to release the blockage causing the ischemia.

NO is also an active neurotransmitter. Excessive production or activity of NO may result in neurological diseases, particularly those affecting the brain. Therefore, administration of the composition used in the method of the invention can treat neurological diseases. To facilitate crossing of the blood-brain barrier, if the composition is administered intravenously, the chitosan or derivatives thereof can be covalently linked to hydrophobic moieties or proteins that are known to cross the barrier. Alternatively, the composition can be administered intracranially or intraventricularly.

Chitin can be manufactured by the deproteination and decalcification of crab or shrimp shells (see, e.g., U.S. Pat. No. 3,903,268). Chitosan can then be obtained by deacetylating chitin with a hot alkali solution. Alternatively, chitin can be isolated from various fungal species, such as from a member of the genus Actinomucor. In addition, chitosan and derivatives thereof are available from known chemical vendors such as Sigma Chemical Co. (St. Louis, Mo.). Any preparation of chitosan should be tested to ensure that no detectable endotoxin is present in the preparation.

The composition of the present invention can be administered via any appropriate route, e.g. intravenously, intraarterially, topically, by injection, intraperitoneally, intrapleurally, orally, subcutaneously, intramuscularly, sublingually, intraepidermally, or rectally. It can be formulated as a solution, suspension, suppository, tablet, granules, powder, capsules, ointment, or cream. In the preparation of these compositions, a solvent (e.g., water or physiological saline), solubilizing agent (e.g., ethanol, Polysorbates, or Cremophor EL7), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane can be added. Pharmaceutical preparations such as solutions, tablets, granules or capsules can be formed with these components.

Chitosan or its derivatives can also be delivered in a composition that includes another drug. See, e.g., Knapczyk et al., "Pharmaceutical Dosage Forms with Chitosan," In: Chitin and Chitosan, Skjak-Braek et al., eds., Elsevier Applied Science, 1998, pp 665–669. This study and others, as well as the example below, indicate or suggest that chitosan and its derivatives are well tolerated and not cytotoxic in vivo. Thus, dosages of chitosan or derivatives thereof can be increased to effective levels within reason with little worry of toxicity.

The specific dose of the composition of the present invention is determined in consideration of the results of animal experiments and various conditions. More specific doses obviously vary depending on the administration method; the condition of the subject such as age, body weight, sex, sensitivity, food eaten, dosage intervals, medicines administered in combination; and the source, seriousness, and degree of NO-induced abnormality. The optimal dose and the administration frequency under a given condition must be determined by the appropriate dosage test of a medical specialist based on the aforementioned guide.

It is generally useful to test the efficacy of compositions, materials, or medical devices containing chitosan or derivatives thereof, before administering the composition into a human patient. For example, chitinous compositions can be tested for its ability to aid healing or treat a number of conditions in calves or cows as described in Minami et al., "Application of Chitin and Chitosan in Large Animal Practice," In: *Advances in Chitin and Chitosan*, Brine et al., eds., Elsevier Applied Science, New York, 1992, pp 61–69. Efficacy testing in small animals can be similarly accomplished as described in Okamoto et al., "Application of Chitin and Chitosan in Small Animals," In: *Advances in Chitin and Chitosan*, Brine et al., eds., Elsevier Applied Science, New York, 1992, pp 70–78; Johnson et al., "In vivo Tissue Response to Implanted Chitosan Glutamate," In: *Advances in Chitin and Chitosan*, Brine et al., eds., Elsevier Applied Science, pp 3–8, 1992; or Su et al., Biomaterials 18:1169–1174, 1997. For wound healing studies, the chitosan or its derivatives can be formed into surgical prosthetic sheets that are then used, for example, to close a hernia or replace a patch of skin. See Su et al., supra; Austin et al., Science 212:749–753, 1981; Su et al., Biomaterials 20:61–68, 1999; and Kifune, "Clinical Application of Chitin Aritificial Skin (Beschitin W), In: *Advances in Chitin and Chitosan*, Brine et al., eds., Elsevier Applied Science, pp 9–15, 1992. Alternatively, chitosan or its derivatives can be used to manufacture sutures that aid healing or decrease inflammation. See, e.g., Tachibana et al., Jap. J. Surg. 18:533–539, 1988; and Biagini et al., "Biological Materials for Wound Healing," In: *Advances in Chitin and Chitosan*, Brine et al., eds., Elsevier Applied Science, pp 16–24, 1992. These testing procedures can be readily modified to specifically detect the amount of NO in tissue biopsies or an implanted device at the affected site by using known methods or the assays described in the example below.

Without further elaboration, it is believed that one skilled in the art can, based on the above disclosure and the description below, utilize the present invention to its fullest extent. The following examples are to be construed as merely illustrative of how one skilled in the art can practice the invention and are not limitative of the remainder of the disclosure in any way. Any publications cited in this disclosure are hereby incorporated by reference.

EXAMPLES

The NO-inhibiting activity of chitosan and derivatives thereof was discovered using the following materials and methods.

Cell Culture.

NIH/3T3 (mouse embryo fibroblast, CCRC 60008) and RAW 264.7 (mouse monocyte/macrophage, CCRC 60001) cell lines were obtained from Culture Collection and Research Center (CCRC), Taiwan. Both cell lines were cultured in Dulbecco's modified essential medium (DMEM, GIBCO BRL, Rockville, Md.) containing 1.5 g/L $NaHCO_3$ supplemented with 10% fetal bovine serum (Hyclone, Logan, Utah) and incubated in 5% $CO_2$ at 37° C. Cell cultures were examined for mycoplasma contamination with the fluorescent stain Hoechst 33258 (Hay et al., ATCC Quality Control Methods for Cell Lines, American Type Culture Collection, Manassas, Va., 1992, pp 23–33). All cultures described in the present example were mycoplasma-free.

Collagen/Chitin-Coated Wells.

Two mixtures were prepared. A mixture of collagen type I (rat tail, Sigma, St. Louis, Mo.) was dissolved in 0.1 N acetic acid to produce a 1 mg/ml collagen solution. Chitin was added to 0.1 N acetic acid until a 1 mg/ml mixture was achieved, and the mixture was sonicated for 3 minutes using a Labsonic U sonicator, (Braun Biotech International, Germany). After being autoclaved at 121° C. for 15 minutes, the chitin mixture became a slurry of fine wires. Microtiter tissue culture plates (96-well) were rinsed with Dulbecco's phosphate-buffer saline without $Ca^{+2}$ and $Mg^{+2}$ (D-PBS, GIBCO BRL). Five microliters of collagen solution or different amounts of the chitin mixture were then added to each well. The plates were then air-dried in a laminar flow hood and stored at 4° C. for up to a week.

Cytotoxicity Test.

For chitin cytotoxicity experiment, cells were subcultured in 96-well tissue culture plates precoated with different amount of chitin or with collagen at a density of 2000 cells/well and incubated for 48 hours. For chitosan cytotoxicity experiment, cells were subcultured in the coated 96-well tissue culture plates and incubated overnight. The next day, culture media were discarded and replaced with fresh media containing different amount of chitosan. The cultures where then incubated for an additional 48 hours. Cytotoxicity was measured using the dye 3-(4,5-dimethylthiazol-2-yl)-2,5-diphenyl tetrazolium bromide (MTT; Merck Co., Germany) and following the methods described in Mosmann, J. Immunol. Methods 65:55–63, 1983.

Measurement of NO Production via Nitrite Detection.

Nitric oxide (NO) production was indirectly quantified by measuring the accumulation of nitrite ($NO_2^-$) in the culture media using Griess reagents and sodium nitrite as a standard (Green et al., Anal. Biochem. 126:131–138, 1982; and Ignarro et al., Proc. Natl. Acad. Sci. USA 90:8103–8107, 1993). For nitrite assays, RAW 264.7 cells were subcultured in coated 96-well tissue culture plates at $1 \times 10^5$ cells/well and incubated for 24 hours. The culture media were changed to phenol red-free, serum-free DMEM containing 100 U/ml interferon-γ(IFN-γ, recombinant murine; GIBCO BRL) and 100 ng/ml lipopolysaccharide (LPS, Escherichia coli serotype 0128:B12; Sigma). The samples were then tested as described in Rollo et al., J. Leukoc. Biol. 60:397–404, 1996.

To measure the effect of chitin on NO production, cells were subcultured directly in the chitin-coated 96-well tissue culture plates. After overnight incubation, cells became adhered to the bottom of chitin-coated wells. The culture media were removed and replaced with media supplemented with IFN-γ and LPS as described above. After 48 hours incubation, 50 ml of culture supernatants were mixed sequentially with equal volumes of 60 mM sulfanilamide (Sigma) in 3 N HCl and 4 mM N-1-naphthylethylenediamine (Sigma) and then shaken for 5 minutes at room temperature as described in Rollo et al., supra. Nitrite concentration was measured by reading the sample's absorbance at 540 nm using a microplate reader (MRX, Dynex Technologies, Inc., VA).

Other Chemicals.

Chitin (MW about 450 kDa) and chitosan (MW about 150 kDa, 95% deacetylated) were obtained from Sun-Chiu Chemical Co., Taiwan. Glucosamine and N-acetylglucosamine were purchased from Sigma Chemical Co. Chitobiose (2-acetamido-2-deoxy-4-O-(2-acetamido-2-deoxy-b-D-glucopyranosyl)-D-glucopyranose), chitotriose, chitotetraose, chitopentose, and chitohexose were purchased from Calbiochem Co. (La Jolla, Calif.).

The cytotoxicity associated with chitin and chitosan was evaluated for both mouse embryonic fibroblast NIH/3T3 cells and mouse monocyte-macrophage RAW 264.7 cells. Different volumes of chitin slurry solution were added and air-dried on the 96-well tissue culture plates before cells were seeded and adhered thereto. After 48 hours incubation, cell growth was assayed by using MTT dye. When 1 to 2 μl of the 1 mg/ml chitin mixture was added to a well, chitin increased the growth of RAW 264.7. NIH/3T3 cell growth was increased when 1 μl was added to a well. Above these dosages for the respective cell types, chitin inhibited cell growth in a dose-dependent manner, up to 20 μl added per well. However, even at the 5 μl/well dose, cell growth was reduced by only about 10%, indicating that the experimental conditions used below did not substantially inhibit cell growth.

Chitosan did not elicit any measurable cytotoxicity in NIH/3T3 cells at a dose up to 200 μg/ml chitosan in the culture medium. It was also noted that a low concentration of chitosan (0.32 μg/ml) promoted growth of RAW 264.7 cells, while concentrations of chitosan above 8 μg/ml slightly inhibited RAW 264.7 cell growth.

Macrophage RAW 264.7 cells can be stimulated with IFN-γ or LPS to produce NO (Rollo et al., supra). However, chitosan suppressed NO production (measured as nitrite) in IFN-γ and LPS activated RAW 264.7 cells in a dose-dependent manner, up to 200 μg/ml. At the highest dosage (200 μg/ml), NO production was reduced by about 85%. Similarly, NO production in activated RAW 264.7 cells was reduced by about 52% when plated on coated tissue culture plates supplemented with 5 μl/well chitin. The NO inhibition results are summarized in Table 1 below.

TABLE 1

| Supplement to Culture Medium (each well) | Nitrite Production (μM) | Nitrite Production as Percentage of Control |
|---|---|---|
| None (control) | 74.0 ± 1.2 | 100 |
| 5 μl Collagen | 73.4 ± 0.9 | 99 |
| 5 μl Chitin | 38.5 ± 0.8 | 52 |
| 5 μl Chitin + 2 μg/ml chitosan | 24.0 ± 2.2 | 32 |
| 5 μl Chitin + 10 μg/ml chitosan | 21.4 ± 1.4 | 29 |

As can be seen in Table 1, collagen-coated wells did not significantly affect NO production in activated RAW 264.7 cells, while chitin and/or chitosan significantly reduced NO production.

To test whether derivatives of chitin, or monomers of chitin and chitosan, also reduced NO production, activated RAW 264.7 cells were cultured in the presence of N-acetylglucosamine (NAGA; the monomeric unit of the chitin polymer), glucosamine (the monomeric unit of chitosan), and oligosaccharide derivatives of chitin. The results are summarized in Table 2 below.

TABLE 2

| Supplement to Culture Medium (each well) | Nitrite Production (μM) | Nitrite Production as Percentage of Control |
|---|---|---|
| None (control) | 65.6 ± 0.7 | 100 |
| 10 μg/ml NAGA | 66.7 ± 0.9 | 102 |
| 10 μg/ml glucosamine | 64.3 ± 0.8 | 98.0 |
| 2 μg/ml chitobiose | 64.9 ± 0.8 | 98.9 |
| 10 μg/ml chitobiose | 64.1 ± 0.9 | 97.7 |
| 2 μg/ml chitotriose | 61.5 ± 0.9 | 93.8 |
| 10 μg/ml chitotriose | 61.1 ± 0.2 | 93.1 |
| 2 μg/ml chitotetraose | 63.4 ± 0.5 | 96.6 |
| 10 μg/ml chitotetraose | 61.3 ± 0.6 | 93.4 |
| 2 μg/ml chitopentose | 47.0 ± 0.5 | 70.6 |
| 10 μg/ml chitopentose | 42.7 ± 1.2 | 65.1 |

TABLE 2-continued

| Supplement to Culture Medium (each well) | Nitrite Production ($\mu$M) | Nitrite Production as Percentage of Control |
|---|---|---|
| 2 $\mu$g/ml chitohexose | 41.3 ± 0.8 | 63 |
| 10 $\mu$g/ml chitohexose | 35.8 ± 2.9 | 54.5 |

As seen in Table 2, chitin and chitosan monomers, as well as short (1–3 residues) oligosaccharide derivatives of chitin did not substantially affect NO production in activated RAW 264.7 cells. However, longer oligosaccharide derivatives (chitopentose and chitohexose) did substantially decrease NO production, with chitohexose being a more potent inhibitor than chitopentose. Note that glucosamine, NAGA, and all tested oligosaccharide derivatives of chitin were not cytotoxic to RAW 264.7 cells, as determined using the cytotoxicity procedures described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A method of reducing nitric oxide production in a subject, the method comprising
    identifying a subject in which reduction of nitric oxide production is desired; and
    administering to the subject an endotoxin-free composition comprising chitosan in an amount sufficient to reduce nitric oxide production in the subject,
wherein the chitosan is a polymer of 5 or more glucosamine residues.

2. The method of claim 1, wherein the chitosan in the composition is partially acetylated.

3. The method of claim 1, wherein the chitosan in the composition is fully acetylated.

4. The method of claim 3, wherein the chitosan is a polymer of 5 to 10 glucosamine residues.

5. The method of claim 4, wherein the chitosan is a polymer of 5 glucosamine residues.

6. The method of claim 4, wherein the chitosan is a polymer of 6 glucosamine residues.

7. The method of claim 1, wherein the chitosan is a polymer of 5 to 10 glucosamine residues.

8. The method of claim 7, wherein the chitosan is a polymer of 5 glucosamine residues.

9. The method of claim 7, wherein the chitosan is a polymer of 6 glucosamine residues.

10. The method of claim 1, wherein the composition is administered at a site of inflammation in the subject.

11. The method of claim 1, wherein the composition is administered in an implantable device.

12. The method of claim 1, wherein the composition is administered systemically to the subject.

13. The method of claim 1, wherein the composition is administered locally to the subject.

14. A method of reducing nitric oxide production in a cell, the method comprising contacting the cell with an endotoxin-free composition comprising chitosan in an amount sufficient to reduce nitric oxide production in the cell, wherein the chitosan is a polymer of 5 or more glucosamine residues.

15. The method of claim 14, wherein the chitosan in the composition is partially acetylated.

16. The method of claim 14, wherein the chitosan in the composition is fully acetylated.

17. The method of claim 16, wherein the chitosan is a polymer of 5 to 10 glucosamine residues.

18. The method of claim 17, wherein the chitosan is a polymer of 5 glucosamine residues.

19. The method of claim 17, wherein the chitosan is a polymer of 6 glucosamine residues.

20. The method of claim 14, wherein the chitosan is a polymer of 5 to 10 glucosamine residues.

* * * * *